(12) United States Patent
Stoerkel et al.

(10) Patent No.: US 9,579,175 B2
(45) Date of Patent: Feb. 28, 2017

(54) ORAL-HYGIENE IMPLEMENT AND ORAL-HYGIENE DEVICE COMPRISING AN ORAL-HYGIENE IMPLEMENT

(71) Applicant: Braun GmbH, Kronberg (DE)

(72) Inventors: Ulrich Stoerkel, Bad Nauheim (DE); Thomas Fritsch, Eppstein (DE)

(73) Assignee: BRAUN GMBH, Kronberg (DE)

( * ) Notice: Subject to any disclaimer, the term of this patent is extended or adjusted under 35 U.S.C. 154(b) by 170 days.

(21) Appl. No.: 14/489,546

(22) Filed: Sep. 18, 2014

(65) Prior Publication Data

US 2015/0082561 A1    Mar. 26, 2015

(30) Foreign Application Priority Data

Sep. 25, 2013   (EP) .................................... 13186042

(51) Int. Cl.
*A61C 17/34*   (2006.01)
*A61C 17/22*   (2006.01)

(52) U.S. Cl.
CPC ......... *A61C 17/222* (2013.01); *A61C 17/3418* (2013.01)

(58) Field of Classification Search
CPC ... A61C 17/34; A61C 17/3418; A61C 17/349; A61C 17/3409
See application file for complete search history.

(56) References Cited

U.S. PATENT DOCUMENTS

| | | | |
|---|---|---|---|
| 5,177,826 A | 1/1993 | Vrignaud et al. | |
| 6,813,793 B2 * | 11/2004 | Eliav .................... | A61C 17/349 15/22.1 |
| 7,392,562 B2 * | 7/2008 | Boland ................... | A46B 7/06 15/22.1 |
| 2004/0060133 A1 | 4/2004 | Eliav | |
| 2005/0132513 A1 | 6/2005 | Eliav et al. | |

FOREIGN PATENT DOCUMENTS

WO   WO 2004/028390 A2   4/2004
WO   WO 2006/029395 A1   3/2006

OTHER PUBLICATIONS

European Search Report dated Feb. 11, 2014; 4 pages.

* cited by examiner

*Primary Examiner* — Laura C Guidotti

(57) ABSTRACT

An oral-hygiene implement having a housing, a first carrier on which at least one first oral-treatment element is mounted, a second carrier on which at least one second oral-treatment element is mounted, wherein at least the first carrier element is mounted for driven oscillatory movement with a peak amplitude value relative to the housing and wherein the first and second oral-treatment elements are arranged such that the first oral-treatment element contacts the second oral-treatment element at least once during each oscillation period of the first carrier at a contact amplitude value smaller than the peak amplitude value and moves the second oral-treatment element out of its initial position until the peak amplitude value is reached.

16 Claims, 7 Drawing Sheets

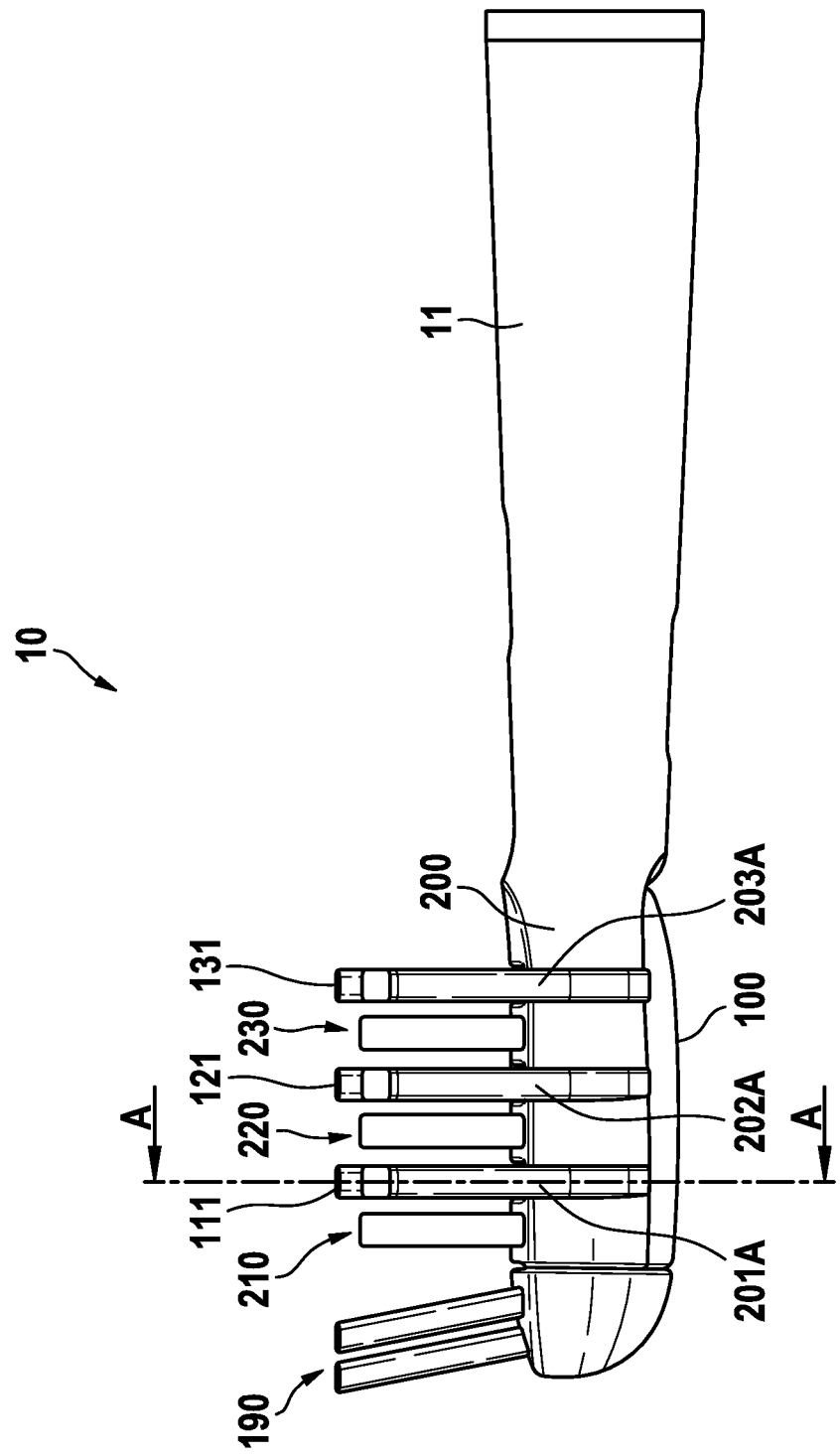

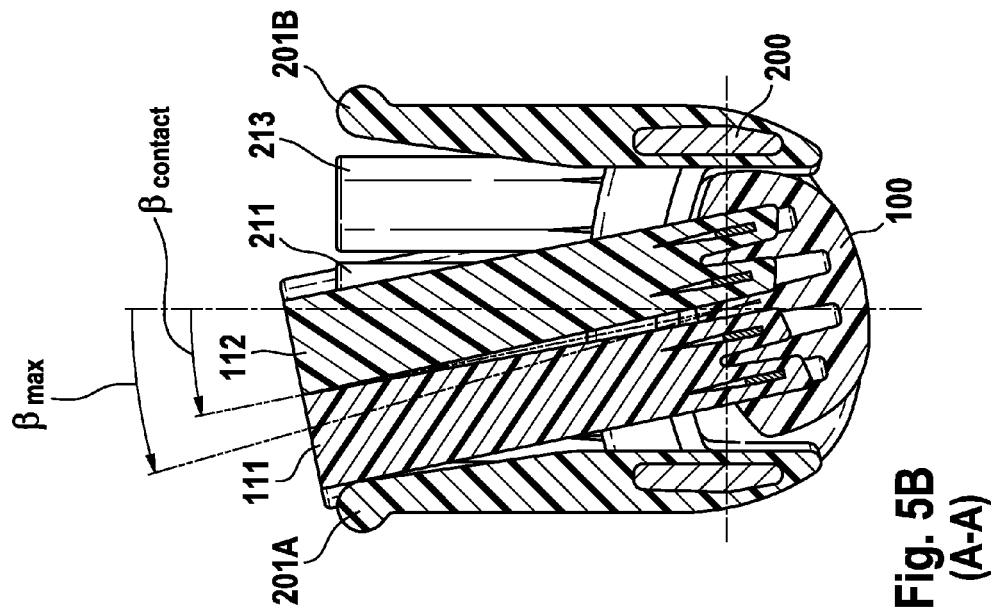
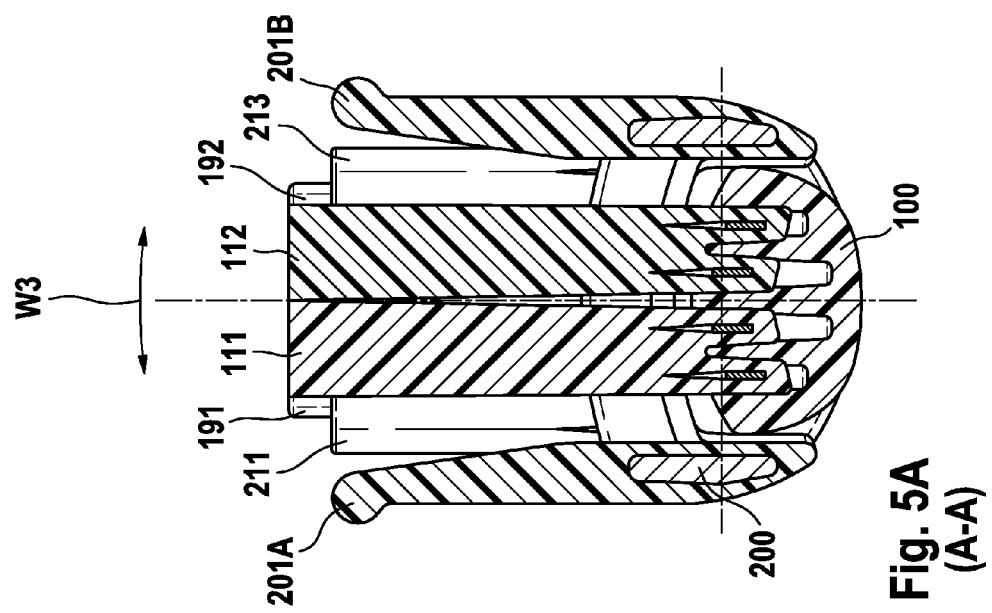

ORAL-HYGIENE IMPLEMENT AND ORAL-HYGIENE DEVICE COMPRISING AN ORAL-HYGIENE IMPLEMENT

FIELD OF THE INVENTION

The present invention is concerned with oral-hygiene implements and in particular with oral-hygiene implements that have a first carrier on which at least one first oral-treatment element is mounted and a second carrier on which at least one second oral-treatment element is mounted.

BACKGROUND OF THE INVENTION

It is known that an oral-hygiene implement such as a toothbrush head has cleaning elements for cleaning the teeth and/or for massaging and stimulating soft tissue (e.g. the gums). Toothbrush heads are known, where a cleaning element carrier is mounted for driven oscillating rotation, where bristle tufts as well as elastomeric elements are mounted on the carrier (e.g. the Oral-B® FlossAction™ brush head, where the elastomeric elements are further pivotably mounted on the carrier so that they can pivot due to acceleration forces acting on the elastomeric elements). Other toothbrush heads are known that have cleaning elements mounted on a carrier that is intended for driven movement and further cleaning elements that are mounted on a further carrier that is intended to remain static with respect to the toothbrush head housing (e.g. the Oral-B® TriZone/Deep Sweep brush head).

It is an object of the present disclosure to provide an oral-hygiene implement that provides additional function over the known brush heads.

SUMMARY OF THE INVENTION

In accordance with one aspect there is provided an oral-hygiene implement having a housing, a first carrier on which at least one first oral-treatment element is mounted, a second carrier on which at least one second oral-treatment element is mounted, wherein at least the first carrier is mounted for driven oscillatory movement with a peak amplitude value relative to the housing and wherein the first and the second oral-treatment elements are arranged such that the first oral-treatment element contacts the second oral-treatment element at least once during each oscillation period of the first carrier at a contact amplitude value smaller than the peak amplitude value and moves the second oral-treatment element out of its initial position until the peak amplitude value is reached.

In accordance with one aspect there is provided an oral hygiene device comprising an oral-hygiene implement as proposed.

BRIEF DESCRIPTION OF THE DRAWINGS

The present disclosure will be further elucidated by a description of general aspects of the proposed oral-hygiene implement as well as by a detailed description of example embodiments and with reference to figures. In the figures

FIG. 3B is a side view onto the oral-hygiene implement shown in FIG. 2;

FIG. 5A is a cross sectional cut through a head section of the oral-hygiene implement shown in FIG. 2;

FIG. 5B is the same cross sectional cut as shown in FIG. 5A but at a different deflection stage of the first carrier with respect to the second carrier.

DETAILED DESCRIPTION OF THE INVENTION

Figure 1A:
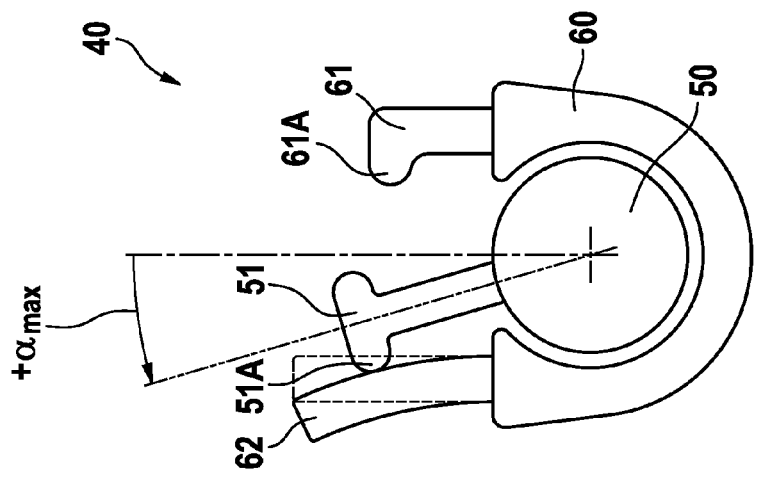
FIG. 1A is a schematic depiction of a cross section cut through a head section of an example embodiment of an oral-hygiene implement having a first and a second carrier in accordance with the present disclosure, where the first carrier is mounted for driven oscillatory movement.

In general terms, an oral-hygiene implement in accordance with the present disclosure provides for additional function as at least one first oral-treatment element (mounted on a first carrier that is driven into an oscillatory motion having a peak amplitude value) contacts at least one second oral-treatment element (mounted on a second carrier) at a contact amplitude value of the first carrier smaller than the peak amplitude value and then the first oral-treatment element (which is further moved against the second oral-treatment element until the first carrier reaches its peak amplitude value, after which the direction of the oscillatory motion is reverted) applies a force onto the second oral-treatment element and moves this second oral-treatment element from an initial position into a bent or deflected position. Due to the oscillatory motion of the first carrier, this contact happens at least once during a period of the oscillatory motion.

The first and second oral-treatment elements may each be realized as a bristle tuft or as an elastomeric element, while this should not exclude other realizations, e.g. in some embodiments the second oral-treatment element may be realized as a relatively rigid element that is pivotably mounted. In some embodiments, a further first oral-treatment element is present, which may either also be arranged to contact, apply a force and then move the same second oral-treatment element and/or may be arranged to contact, apply a force and then move a further (i.e. different) second oral-treatment element. The oral-treatment elements are arranged such that the contact of the first and second oral-treatment element happens periodically at least once in a period, in particular periodically with the same frequency as the driving frequency with which the first carrier (and thus the first oral-treatment element) is driven into motion. While the driven oscillatory movement happens between amplitude values in the range of $[-\alpha_{max}, +\alpha_{max}]$, here $|\alpha_{max}|$ is the peak amplitude value of the oscillatory movement, the first oral-treatment element may contact the second and a further second oral-treatment element at different (absolute) contact amplitude values and/or the first oral-treatment element contacts the second oral-treatment element at a different (absolute) contact angle than a further first oral-treatment element contacts a further second oral-treatment element. This shall not exclude that the contact amplitudes have the same (absolute) value.

In some embodiments, at least one third oral-treatment element is present (either mounted on the first or second carrier or mounted an a third carrier) that is arranged so that it does not come into contact with either the first oral-treatment element(s) or the second oral-treatment element(s). In some embodiments, the second oral-treatment element is mounted on a lateral edge of the oral-hygiene implement.

In some embodiments, a first row of first oral-treatment elements is mounted on the first carrier (a row having at least two first oral-treatment elements). The first row of first oral-treatment element may be arranged so that they move in a single plane. A second oral-treatment element may be mounted on one side of the first row of first oral-treatment elements (i.e. extending in the same plane in which the first row of first oral-treatment elements moves so that one of the first oral-treatment elements contacts, applies a force and then moves the second oral-treatment element out of its initial position into a bent position as was previously described) and in some embodiments a further second oral-treatment element is mounted on the opposite side of the row of first oral-treatment elements (i.e. extending in the same plane as the second oral-treatment element so that one other of the first oral-treatment elements contacts, applies a force and thus moves the further second oral-treatment element). In some embodiments, at least one further row of first oral-treatment elements (arranged for being moved in a single plane) is mounted on the first carrier, which further row may in particular be parallel to the first row of first oral-treatment elements. At least one second oral-treatment element may be mounted on at least one side of the further (or second) row of first oral-treatment elements.

FIG. 1A is a schematic cross-sectional cut through an example embodiment of an oral-hygiene implement 40 in accordance with the present disclosure. The oral-hygiene implement 40 has a first carrier 50 mounted for driven oscillatory rotation around a longitudinal axis L1 (which longitudinal axis L1 extends into the paper plane) such that an oscillatory wiping motion of the first carrier 50 is generated in the driven state as indicated by double arrow W1. Generally, the first carrier is moved out its centre position up to a peak amplitude, which here is a peak deflection angle $\alpha_{max}$ (i.e. the first carrier moves periodically between $+\alpha_{max}$ and $-\alpha_{max}$). In other embodiments, the oscillatory motion is an oscillating linear motion and the peak amplitude is a peak elongation position. In case of an oscillatory rotation, the peak amplitude value [$\alpha_{max}$] may lie in a range of about 1 degree to about 90 degrees, optionally in a range of between about 5 degrees to about 50 degrees, further optionally in a range of between 10 degrees to about 30 degrees.

Generally, at least one first oral-treatment element 51 is mounted on the first carrier 50 and is thus mounted for driven oscillatory motion, here oscillatory rotation around the longitudinal axis L1. As the first oral-treatment element 51 extends in a plane that is perpendicular to the longitudinal axis L1, the first oral-treatment element 51 moves during its oscillatory wiping motion in a plane coinciding with the paper plane, i.e. in a plane perpendicular to the longitudinal axis L1. A second carrier 60 here partially envelopes the first carrier 50 and leaves open a window into which the first carrier 50 extends and within which the first oral-treatment element 51 can be moved (generally, a window is not necessary as long as the first and the second carrier can move relatively to each other such that the at least one first oral-treatment element can get in contact with the at least one second oral-treatment element at least once during a cycle of the periodic movement of the first carrier (and thus of the first oral-treatment element). The second carrier 60 may be fixedly mounted with respect to a housing of the oral-hygiene implement 40 or may be made integral with the housing. Alternatively, the second carrier 60 may also be mounted for a driven movement, e.g. into another oscillatory wiping motion as indicated by double arrow W2. A second oral-treatment element 61 is mounted at an edge of the second carrier 60 essentially within the plane in which the first oral-treatment element 51 moves in an active state (the second oral-treatment element may also be slightly displaced from this movement plane of the first oral-treatment element 51 as long as the first and second oral-treatment elements 51, 61 would contact each other at least once during an oscillation period such that the first oral-treatment element 51 applies a force onto the second oral-treatment element 61 to move it out of its initial or rest position as will be explained in more detail further below). Optionally, a further second oral-treatment element 62 may be mounted on an edge of the second carrier 60 opposite to the second oral-treatment element 61. The first or second oral-treatment element 51, 61 may each be realized as a tuft of bristle filaments comprising in the range of between 20 to 100 filaments, even though this shall not be limiting and any other number of filaments may be suitable, that each may have a diameter in the range of between about 0.05 mm to about 0.3 mm, even though this again shall not be considered as limiting. In some embodiments, the first or second oral-treatment element 51, 61 may be realized as an elastomeric element, e.g. made from a thermoplastic elastomer (TPE), a natural or artificial rubber or a silicone. In some embodiments, the elastomeric element may be directly chemically bonded to the first or second carrier, e.g. by an injection molding process by which the elastomeric element is connected with the material of the carrier. This requires that the material of the carrier and the material of the elastomeric element are insofar affine to each other that a reasonable chemical bonding establishes (e.g. a TPE may sufficiently bond with polypropylene (PP), but not as good with polyoxymethylene (POM)). In some embodiments, a connector element may be provided in the carrier having a good affinity to the material of the elastomeric element, while the carrier itself may then be made from a material that does not need to have sufficient affinity with the elastomeric material (a 3-component injection molding process may be used). In some embodiments, the carrier has an undercut into which material of the elastomeric element may extend so that the elastomeric element is additionally or alternatively connected by a form/force fit with the carrier, which also serves to enhance the force necessary to separate the elastomeric element from the carrier. In some embodiments, the first and/or the second oral-treatment element 51, 61 may have a thickened free end 51A or a projection 61A at the free end pointing towards the respective other oral-treatment element in order to support that the oral-treatment elements get into contact with each other. The thickened free end 51A and the projection 61A are shown for illustration purposes only and it is particularly stated that they are optional features.

Figure 1B:
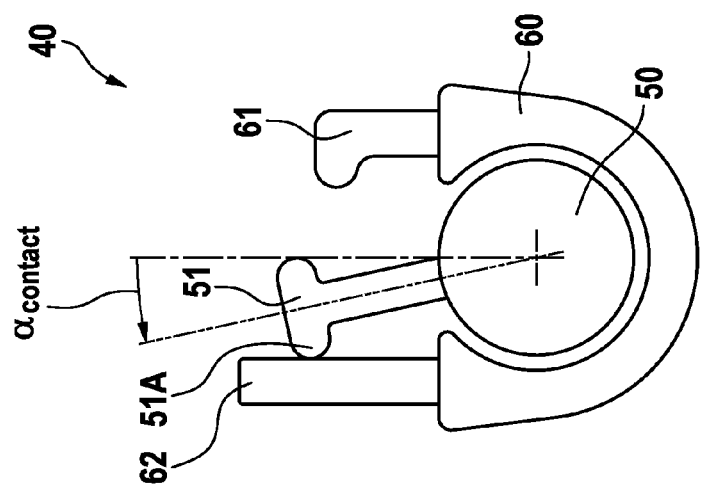
FIG. 1B is the same schematic depiction as FIG. 1A, but where the first carrier carrying a first oral-treatment element is oscillated out of its centre position to a contact amplitude value at which the first oral-treatment element contacts a second oral-treatment element mounted on the second carrier.

FIG. 1B shows a state of the oral-hygiene implement 40 shown in FIG. 1A where the first carrier 50 has reached a contact amplitude value $\alpha_{contact}$ that is absolutely smaller than the peak amplitude value $\alpha_{max}$ of the driven oscillatory motion, i.e. $|\alpha_{contact}|<|\alpha_{max}|$, where the first oral-treatment element 51 contacts the second oral-treatment element 61. In the shown depiction, the first carrier was oscillated into counterclockwise direction relative to the paper plane. As was stated above, in embodiments where the first oral-treatment element (or a further first oral-treatment element mounted on the first carrier) contacts a further second oral-treatment element mounted on the second carrier, the respective absolute contact amplitude value can be different than the absolute value of the contact amplitude between the first and the second oral-treatment elements.

Figure 1C:
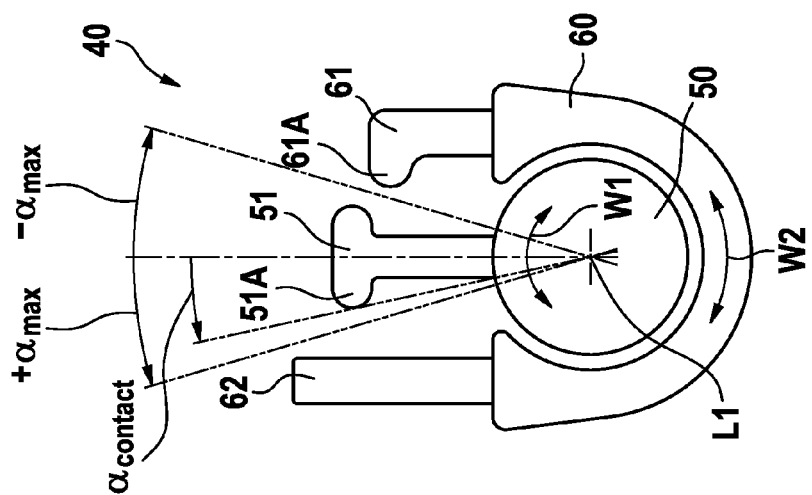
FIG. 1C is the same schematic depiction as FIG. 1B, but where the first carrier is oscillated to its peak amplitude and the first oral-treatment element has moved the second oral-treatment element out of its initial position.

FIG. 1C shows a state of the oral-hygiene implement 40 shown in FIG. 1A where the first carrier 50 has reached its peak amplitude value $\alpha_{max}$ in counterclockwise direction. It can be noted that the first oral-treatment element 51 has in this maximally deflected position already moved the second oral-treatment element 61 out of its initial (or: rest) position shown in FIGS. 1A and 1B. That means that the first oral-treatment element 61 has first come into contact with the second oral-treatment element 61 at a contact amplitude value $\alpha_{contact}$ being absolutely smaller than the peak amplitude value $\alpha_{max}$ (as shown in FIG. 1B) and that by its further movement, the first oral-treatment element 51 has applied a force onto the second oral-treatment element 61 such that the second oral-treatment element 61 is moved into a bent (i.e. deflected) position (it is acknowledged but in the present discussion neglected that also the first oral-treatment element 51 may be deflected due to the physical principle that every action equals an opposite reaction).

For sake of completeness it is stated here, that the contacting and movement of the oral-treatment elements happens due to a geometrical overlap of the oral-treatment elements in their non-deflected states during the oscillatory motion and that the contacting and movement happens independent from a potential additional whipping motion of in particular the free end of the first (or second) oral-treatment element that may occur due to the inertia of the free end during a fast oscillatory motion. Obviously, the contact between oral-treatment elements due to only such a whipping motion happens after the first carrier had reached its peak amplitude value. This means that the first and second oral-treatment elements are arranged such that they contact each other and that the second oral-treatment element is moved into a bent position independent from the frequency of the oscillatory movement (i.e. independent from the velocity with which the first oral-treatment element is moved).

Thus, even though the second carrier 60 may in this example embodiment not be driven into a motion, the first oral-treatment element 51 actively generates a movement of the second oral-treatment element 61 once per cycle of the oscillatory motion into which the first carrier is driven, i.e. if the frequency of the oscillatory motion is 100 Hz, the frequency of the movement of the second oral-treatment element 61 is as well 100 Hz. Obviously, the first carrier may be driven with any other frequency, in particular a frequency in the range of between 50 Hz and 500 Hz.

Optionally, the second carrier 60 may also be driven into a motion, e.g. also an oscillatory motion such as an oscillatory wiping motion around the longitudinal axis L1 as is indicated by double arrow W2 in FIG. 1A.

In an embodiment, where also a further second oral-treatment element 62 is mounted at the second carrier 60 (here: at an edge of the second carrier opposite to the edge where the second oral-treatment element 61 is mounted), the first oral-treatment element 51 may contact and deflect the further second oral-treatment element 62 in every other half-cycle after it has contacted and deflected the second oral-treatment element 61. Thus, it is stated that the further second oral-treatment element 62 shown in FIGS. 1A-1C is purely optional.

While an oscillatory wiping motion of the first carrier is discussed here, this should not be considered as limiting, as in principle all kind of oscillatory movements are contemplated (e.g. an oscillatory linear motion or an oscillatory rotation around a rotation axis that coincides with the longitudinal extension direction of the first oral-treatment elements etc.).

Figure 2:
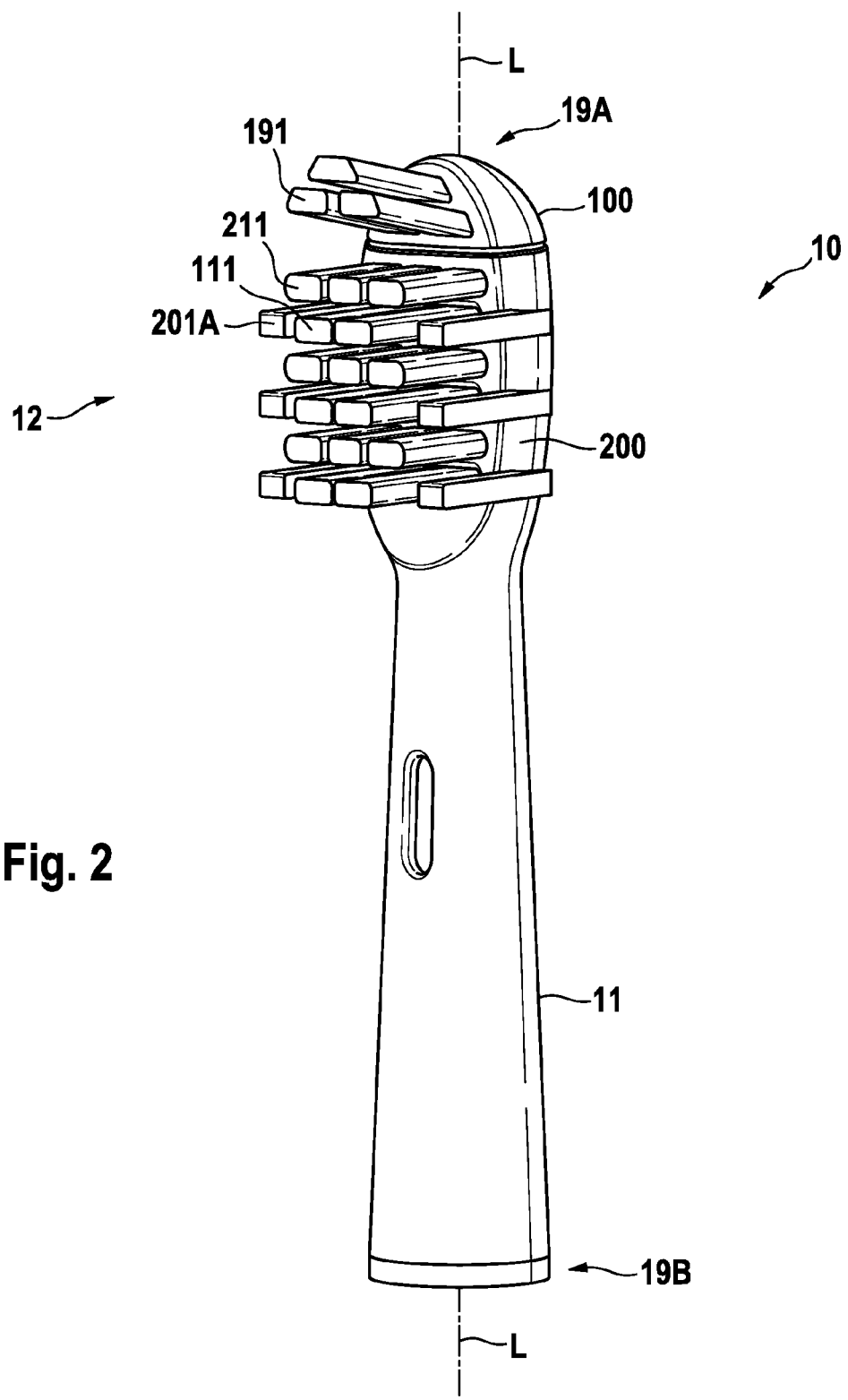
FIG. 2 is a perspective depiction of another example embodiment of an oral-hygiene implement having a first and a second carrier in accordance with the present disclosure.
Figure 6:
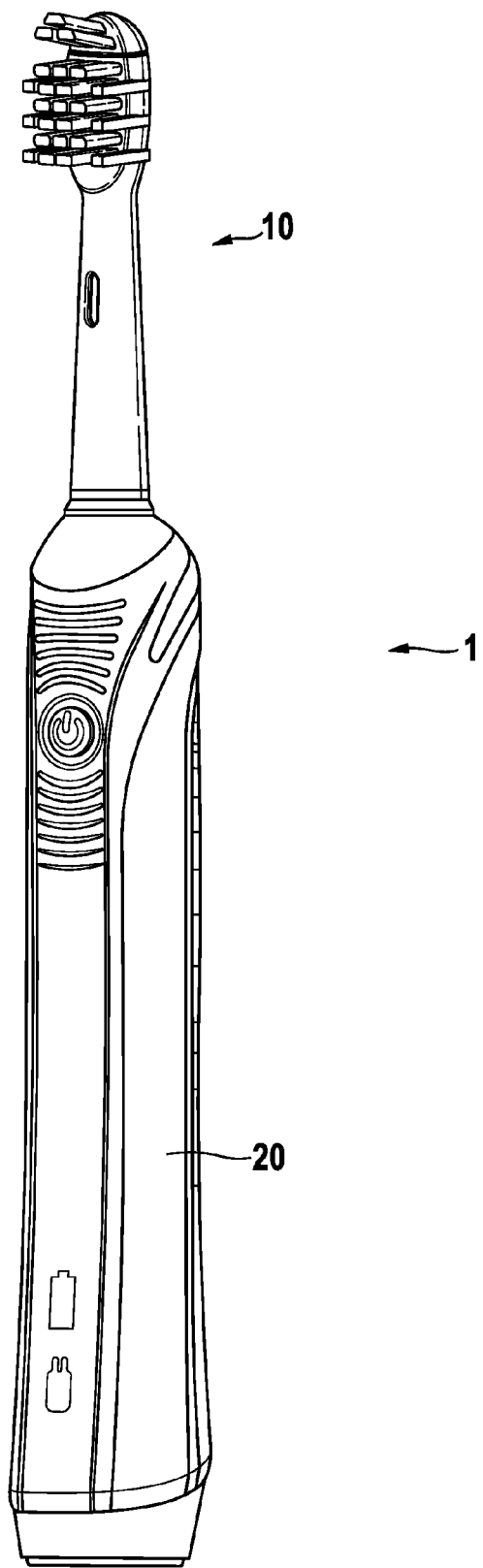
FIG. 6 is a perspective depiction of an example embodiment of an oral hygiene device comprising an oral-hygiene implement as proposed.

FIG. 2 is a perspective depiction of an example embodiment of an oral-hygiene implement 10 in accordance with the present disclosure. The oral-hygiene implement 10 is in the shown example embodiment realized as a replaceable toothbrush head, but this should not be interpreted as limiting. The oral-hygiene implement 10 generally has a housing 11 and a head section 12, where a first carrier 100 is disposed on which at least a first oral-treatment element 111 is mounted. The first carrier 100 is movably mounted at the housing 11 for driven oscillatory motion. In some embodiments, the driven oscillatory motion is an oscillatory wiping motion around a longitudinal axis L of the oral-hygiene implement 10. The longitudinal axis L may in particular extend from the distal end 19A of the oral-hygiene implement 10 to its proximal end 19B (where the terms distal and proximal are here chosen with respect to a handle to which the oral-hygiene implement 10 is intended to be attached—see FIG. 6) and may further lie in a symmetry plane of the oral-hygiene implement. When attached to a handle as shown in FIG. 6, the longitudinal axis L may coincide with the axis of a drive shaft for providing the motion to drive the first carrier. The oral-hygiene implement 10 further comprises a second carrier 200 that in some embodiments is integral with the housing 11 or that is fixedly connected with the housing 11. Generally, at least one second oral-treatment element 201A is mounted on the second carrier 200. In some embodiments, at least one third oral-treatment element 191 or 211 is mounted on either the first carrier or the second carrier, which third oral-treatment element is arranged such that is essentially does not contact any of the at least one first or at least one second oral-treatment elements during operation of the oral-hygiene implement.

Figure 3A:
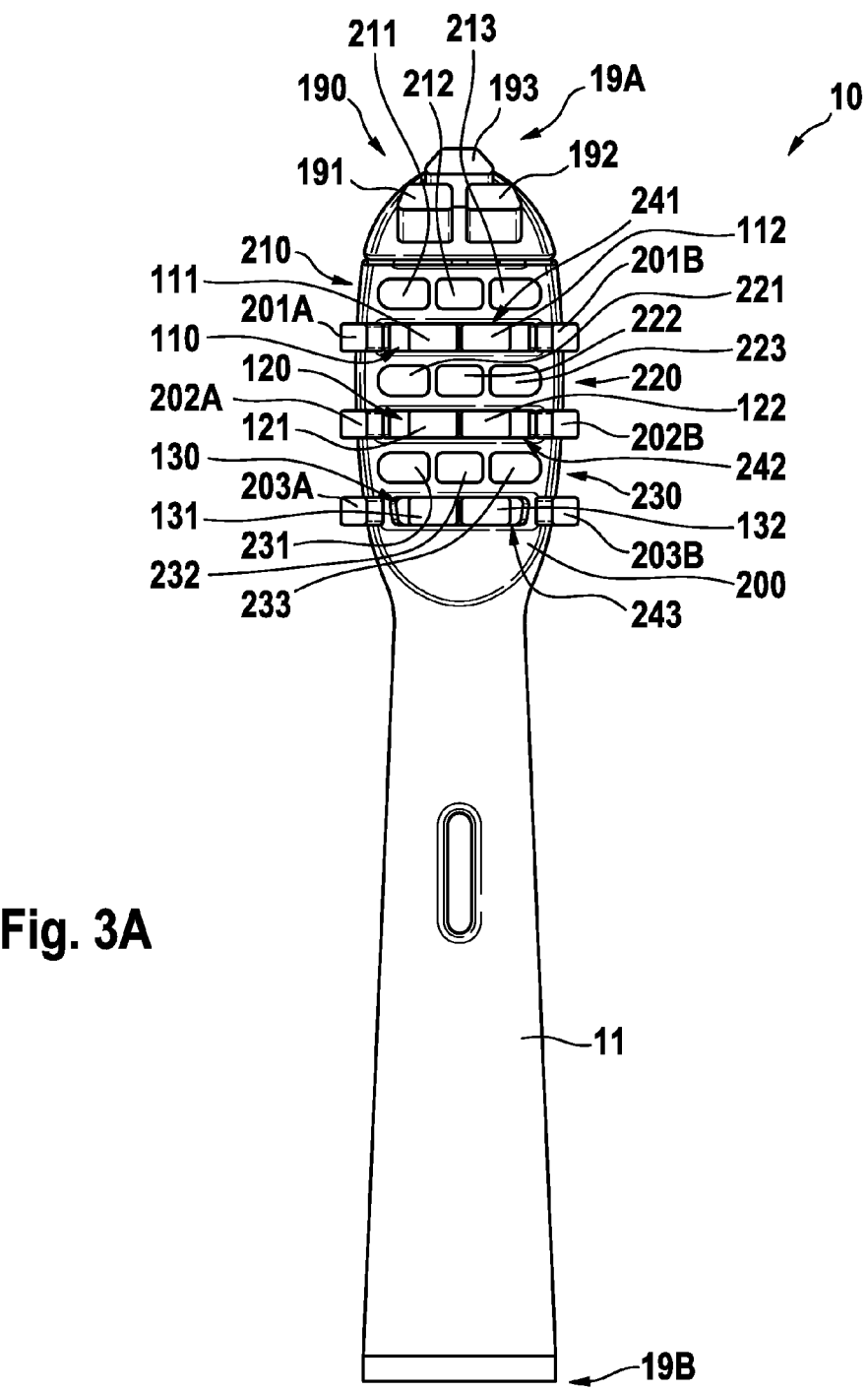
FIG. 3A is a top-down view onto the oral-hygiene implement shown in FIG. 2.

With reference to FIG. 3A and FIG. 3B, which are a top-down view and a side view, respectively, onto the oral-hygiene implement shown in FIG. 2, the structure of the example oral-treatment element field is discussed. In the shown embodiment, three rows 110, 120, 230 of first oral-treatment elements are mounted on the first carrier. Each of the three rows 110, 120, 230 is arranged in a plane that is perpendicular to the longitudinal axis L of the oral-hygiene implement 10. Each of the three rows 110, 120, 230 has two first oral-treatment elements of essentially rectangular cross section that are side-to-side arranged with their short sides, i.e. two first oral-treatment elements 111 and 112 form the first row 110, two first oral-treatment elements 121 and 122 form the second row 120, and two first oral-treatment elements 131 and 132 form the third row 130. The first carrier 100 is arranged underneath the second carrier 200 at least where the first oral-treatment elements 111, . . . are mounted and each of the rows of first oral-treatment elements 110, 120, 130 extends through a respective aperture 241, 242, and 243 in the second carrier 200. At the lateral edges of each of the apertures 241, 242, 243, a second oral-treatment element is arranged (e.g. mounted using any of the technologies described above if realized as an elastomeric element or, e.g., mounted by means of anchor stapling or by an anchor-free technique is realized as a bristle tuft), i.e. two second oral-treatment elements 201A and 201B are oppositely arranged at the lateral edges of aperture 241, two second oral-treatment elements 202A and 202B are oppositely arranged at the lateral edges of aperture 242, two second oral-treatment elements 202A and 202B are oppositely arranged at the lateral edges of aperture 243. Three rows 210,220, 230 of third oral-treatment elements are alternately arranged with the rows 110, 120, 130 of first oral-treatment elements. Third oral-treatment elements 211, 212, 213 form the first row 210, third oral-treatment elements 221, 222, 223 form the second row 220, and third oral-treatment elements 231, 232, 233 form the third row 230 of third oral-treatment elements. In the shown embodiment, the first carrier 100 also forms the distal end 19A of the oral-hygiene implement 10 and a set 190 of fourth oral-treatment elements 191, 192, 193 is mounted on this portion of the first carrier 100. The number of rows of oral-treatment elements and the number of oral-treatment elements in each row here shown should not be considered as limiting. Each row may comprise one, two, three, four, five etc. oral-treatment elements. The number of rows may be one, two, three, four etc. In some embodiments, no third (or fourth) oral-treatment elements are present. In the shown embodiment, the first, third and fourth oral-treatment elements are realized as bristle tufts and the second oral-treatment elements are realized as elastomeric elements. This should not be interpreted as limiting. Each oral-treatment element may individually be realized as a bristle tuft or as an elastomeric or other non-rigid element, even though the laterally arranged second oral-treatment elements can be used for gum massaging, which traditionally is done by an elastomeric element.

Figure 4:
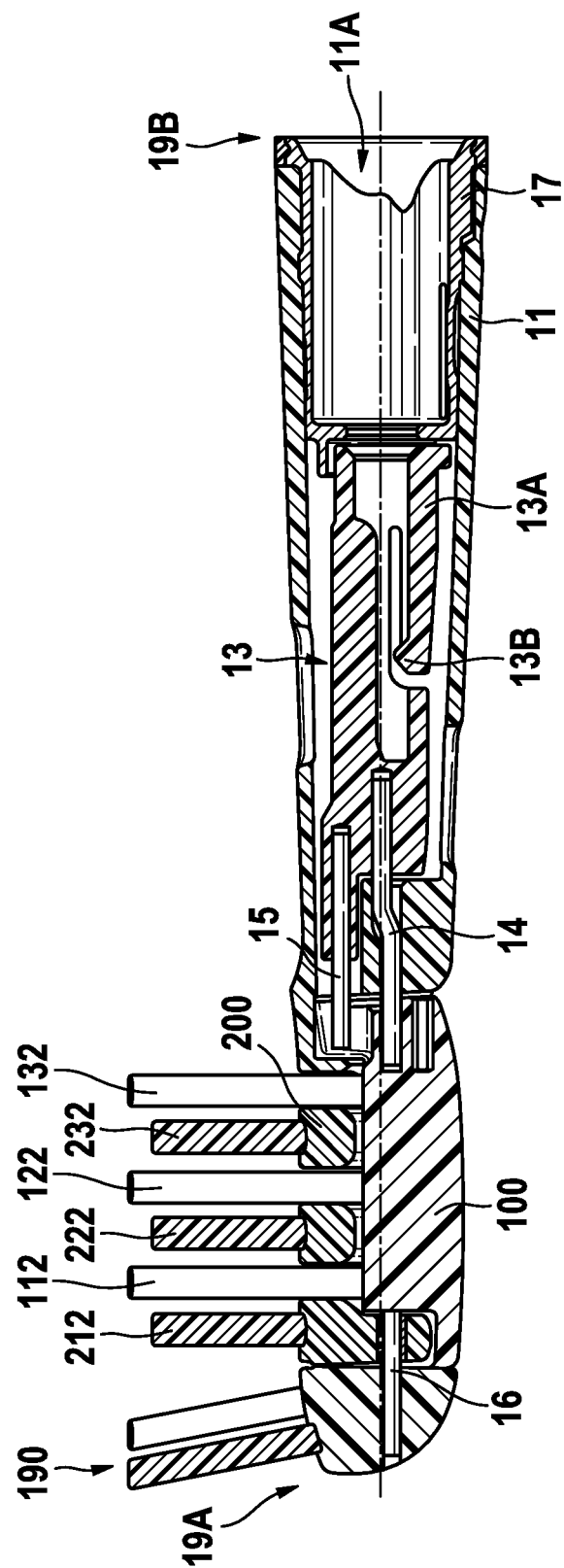
FIG. 4 is a longitudinal cross sectional cut through the oral-hygiene implement shown in FIG. 2.

FIG. 4 is a longitudinal cross sectional cut through the symmetry plane of the oral-hygiene implement shown in FIG. 2. In principle, the design of the shown example oral-hygiene implement 10 despite the additional second oral-treatment elements is similar to the design as described in patent application EP 2 468 214 A1, the relevant content of which is incorporated herein by reference. The example oral-hygiene implement 10 has a generally tubular housing 11 that is hollow. A motion transmitter element 13 may be disposed in the hollow 11A of the tubular housing 11. The motion transmitter element 13 may have a snap hook 13A that is intended to snap with its snap nose 13B into a groove of a drive shaft of a handle for fixation of the motion transmitter element 13. The motion transmitter element 13 is mounted at the housing 11 of the oral-hygiene implement 10 by means of an axle 14 that allows oscillatory rotation of the motion transmitter element 13 around the longitudinal axis L. The first carrier 100 is mounted by means of the axle 14 and a further axle 16 (here, the axle 14 is cranked, which leads to a oscillation axis O of the first carrier 100 that is parallel shifted with respect to the longitudinal axis L). The axle 14 and the further axle 16 may be realized as metal pins, even though, in some embodiments, the axles 14, 16 may be realized as integral projections extending from the motion transmitter 13 and/or the first carrier 100, respectively, and may thus be made from plastic, e.g. made in a plastic injection molding process. The motion transmitter 13 may further comprise an eccentrically mounted tappet element 15 that engages with a respective cavity or cut-out in the first carrier 100, so that the oscillatory rotation provided by the drive shaft of the handle in an attached state of the oral-hygiene implement 10 is transferred via the motion transmitter 13 to the first carrier 100.

FIGS. 5A and 5B are cross sectional cuts taken along a plane indicated by line A-A in FIG. 3A, where FIG. 5A shows the centre position of the first carrier 100 (mounted for driven oscillatory motion as indicated by double arrow W3) and thus of the first row of first oral-treatment elements 111 and 112, while FIG. 3B shows a state in which the first carrier 100 is oscillated to an contact amplitude value $\beta_{contact}$ that is smaller than the peak amplitude value $\beta_{max}$, i.e. $|\beta_{contact}| < |\beta_{max}|$, such that the left first oral-treatment element 111 just gets into contact with the left second oral-treatment element 201A (similar to FIG. 1B). In the present context, "left" or "right" is defined with respect to the paper plane. When the first carrier 100 is moved further in counter-clockwise direction, the left first oral-treatment element 111 applies a force onto the left second oral-treatment element 201A and pushes the left second oral-treatment element 201A into a bent state (as is principally indicated in FIG. 1C). As in the present embodiment the first carrier 100 is driven into an oscillatory wiping motion, the first carrier 100 is moved into clockwise direction after it has reached its peak amplitude value in counter-clockwise direction. In the shown embodiment, then the right (or further) first oral-treatment element 112 will get into contact with the right (or further) second oral-treatment element 201B and, when the first carrier 100 is further moved until it reaches its peak amplitude value in clockwise direction, will apply a force so that the right second oral-treatment element 201B is pushed from its initial (or rest) position into a bent position. The frequency of this oscillatory wiping motion may lie in a range of between about 50 Hz to about 500 Hz, in particular in a range of between about 60 Hz to about 300 Hz. Due to the arrangement of the second oral-treatment elements 201A, 201B, . . . at the lateral edges of the head section 12 of the oral-hygiene implement 10, this arrangement leads to a additional stimulation and massaging of the gums when the oral-hygiene implement 10 is used in its usual manner. Realizing the second oral-treatment elements as elastomeric elements or as tufts made from soft bristles may assist in achieving good stimulation/massaging results as has been mentioned before.

FIG. 6 is a perspective depiction of an oral hygiene device 1 in accordance with the present disclosure. The oral hygiene device 1 is here realized as an electric toothbrush. The oral hygiene device 1 comprises an oral-hygiene implement 10 as previously discussed with reference to FIGS. 2, 3, 4A, and 4B, where generally this is just for sake of illustration purposes and not interpreted to be limiting. The oral hygiene device 1 further has a handle 20. In some embodiments, the oral-hygiene implement 10 and the handle 20 are detachably mounted to each other, i.e. the oral-hygiene implement 10 can be repeatedly detached and again attached to the handle 20 or the oral-hygiene implement 10 can be detached from the handle 20 and could then be replaced by another oral-hygiene implement, e.g. in order to replace a worn-out oral-hygiene implement by another oral-hygiene implement or to just attach another oral-hygiene implement assigned to another user or specific for another oral treatment function (these different functions may include teeth cleaning, teeth polishing, gum massaging, flossing etc.). In some embodiments, the oral-hygiene implement 10 is fixedly connected or integral with the handle 20. The handle 20 may in particular comprise a drive (e.g. a DC motor) for providing a motion and the drive may be coupled to the first carrier of the oral-hygiene implement 10 via a drive shaft.

The drive (potentially including a gear unit) and drive shaft may in particular be arranged for providing an oscillatory motion to the first carrier, e.g. the drive shaft may be arranged to provide an oscillatory rotation around its longitudinal axis or it may provide a linear oscillation along its longitudinal axis.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

What is claimed is:

1. An oral-hygiene implement having a longitudinal axis and comprising:
    a housing;
    a first carrier on which at least one first oral-treatment element is mounted for oscillatory movement around the longitudinal axis of the implement;
    a second carrier on which at least one second oral-treatment element is mounted;
    wherein at least the first carrier element is mounted for driven oscillatory movement with a peak amplitude value relative to the housing and wherein the first oral-treatment element and the second oral-treatment element are arranged such that the first oral-treatment element contacts the second oral-treatment element at least once during each oscillation period of the first carrier at a contact amplitude value smaller than the peak amplitude value and moves the second oral-treatment element out of its initial position until the peak amplitude value is reached.

2. The oral-hygiene implement in accordance with claim 1, wherein the driven oscillatory movement is an oscillatory wiping motion around a longitudinal axis of the oral-hygiene implement such that the free end of the first oral-treatment element is arranged to move essentially along a circular arc around the longitudinal axis.

3. The oral-hygiene implement in accordance with claim 1, wherein the first oral-treatment element comprises a bristle tuft.

4. The oral-hygiene implement in accordance with claim 1, wherein the second oral-treatment element comprises an elastomeric element.

5. The oral-hygiene implement in accordance with claim 1, wherein the second carrier is integral with the housing.

6. The oral-hygiene implement in accordance with claim 1, wherein a further second oral-treatment element is mounted on the second carrier and a further first oral-treatment element is mounted on the first carrier, wherein the further first oral-treatment element is arranged to contact the further second oral-treatment element at least once during each oscillation period of the first carrier at a contact amplitude value smaller than the peak amplitude value and moves the further second oral-treatment element out its initial position until the peak amplitude value is reached.

7. The oral-hygiene implement in accordance with claim 1, wherein the at least one second oral-treatment element is located at a lateral edge of the oral-hygiene implement.

8. The oral-hygiene implement in accordance with claim 7, wherein at least a first row of the first oral-treatment elements is mounted on the first carrier, wherein the first row is arranged to be perpendicular to the longitudinal axis such that during the driven oscillatory wiping motion the first row moves in a plane essentially perpendicular to the longitudinal axis.

9. The oral-hygiene implement in accordance with claim 8, wherein the at least one second oral-treatment element is arranged at a side of the first row essentially within the plane within which the first row moves during the driven movement.

10. The oral-hygiene implement in accordance with claim 9, wherein the at least one second oral-treatment element comprises two second oral-treatment elements, wherein one of the second oral-treatment elements is arranged at the opposite side of the first row in the plane in which the first row moves.

11. The oral-hygiene implement in accordance with claim 10, wherein at least a second row of the first oral-treatment elements is arranged on the first carrier, wherein the second row is parallel to the first row, and wherein the at least one second oral-treatment element is arranged at each side of the second row.

12. The oral-hygiene implement in accordance with claim 1, wherein at least one third oral-treatment element is mounted on the second carrier, wherein the third oral-treatment element is arranged such that it gets into contact with neither the at least one first oral-treatment element nor with the at least one second oral-treatment element.

13. An oral-hygiene device comprising the oral-hygiene implement in accordance with claim 1.

14. The oral-hygiene device in accordance with claim 13, wherein the oral-hygiene implement is arranged for being repeatedly detachable and attachable.

15. The oral-hygiene device in accordance with claim 13, comprising a drive and a drive shaft coupled to the drive, wherein the drive shaft is coupled to the first carrier to transmit movement from the drive to the first carrier.

16. The oral-hygiene implement in accordance with claim 1, wherein the second carrier is fixedly mounted with respect to the housing.

* * * * *